United States Patent [19]

Hagelauer et al.

[11] Patent Number: 4,708,878
[45] Date of Patent: Nov. 24, 1987

[54] PROCESS FOR TEMPERATURE CONTROLLING A LIQUID

[76] Inventors: Ulrich Hagelauer, Magirusstrasse 23, Stuttgart; Uwe Faust, Relenbergstrasse 57, Stuttgart 1, both of Fed. Rep. of Germany

[21] Appl. No.: 719,283
[22] PCT Filed: Jun. 12, 1984
[86] PCT No.: PCT/DE84/00132
  § 371 Date: Jun. 17, 1985
  § 102(e) Date: Jun. 17, 1985
[87] PCT Pub. No.: WO85/00420
  PCT Pub. Date: Jan. 31, 1985

[30] Foreign Application Priority Data

Jul. 13, 1983 [DE] Fed. Rep. of Germany ....... 3325195

[51] Int. Cl.$^4$ .................... G01N 33/02; A23L 3/00
[52] U.S. Cl. ............................ 426/231; 99/451; 426/238; 426/522
[58] Field of Search ............. 426/241, 231, 238, 522; 99/451

[56] References Cited

U.S. PATENT DOCUMENTS

| | | | |
|---|---|---|---|
| 2,585,103 | 2/1952 | Fitzgerald | 99/451 |
| 3,743,523 | 7/1973 | Bodine | 426/238 |
| 3,846,565 | 11/1974 | Rosenberg et al. | 426/238 |
| 4,464,401 | 8/1984 | Kissam | 426/238 |

FOREIGN PATENT DOCUMENTS 1179827  2/1970  United Kingdom .

Primary Examiner—George Yeung
Attorney, Agent, or Firm—Murray and Whisenhunt

[57] ABSTRACT

A method for the temperature control of a liquid and an apparatus to effect such a method wherein the heating of the liquid is carried out by irradiation with acoustic ultrasonic waves. Temperature measurement is effected by a probe immersed in the liquid or by contact-free measurement of infra-red radiation from the liquid. Temperature control is effected by comparison of the measured temperature with a predetermined desired temperature. Since the acoustic ultrasonic heating is thermally inertialess, extreme accuracy of temperature control is possible.

11 Claims, 5 Drawing Figures

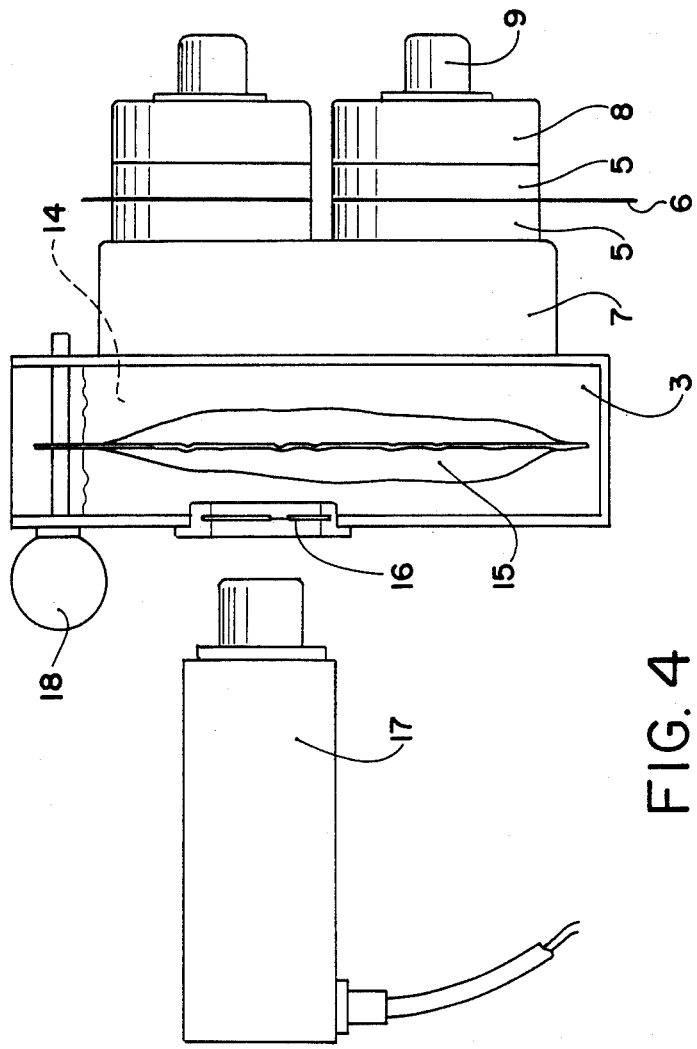
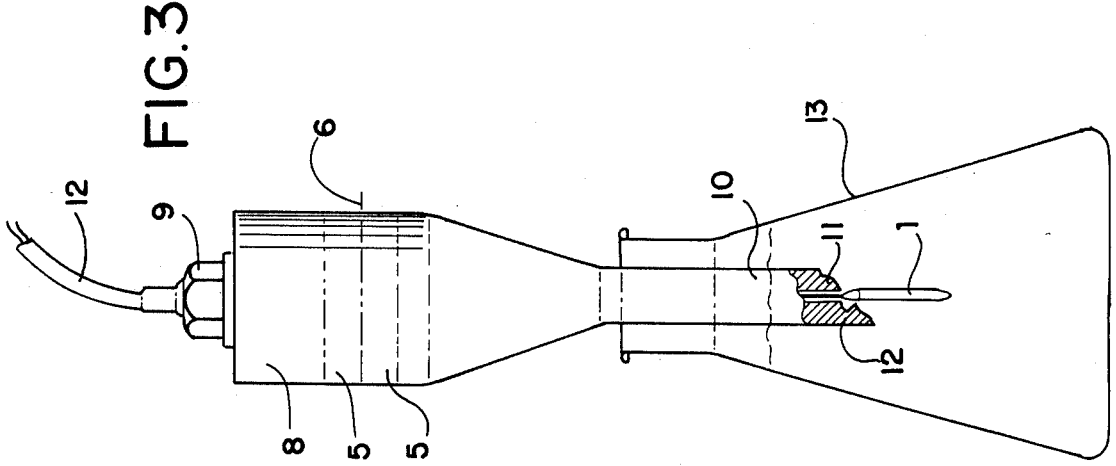
FIG. 4
FIG. 3

PROCESS FOR TEMPERATURE CONTROLLING A LIQUID

STATE OF THE ART

The invention is based on a process for temperature controlling a liquid where this process is of the species stated in the independent claim. In known processes of this type, the liquid temperature controlled is heated either by a heater element projecting directly into the liquid or by a heater element raising the temperature of a container wall and thereby indirectly heating the liquid in the container. Due to this convection heating principle, there arise partial "overheatings", at least until the heat has been distributed uniformly. Quite aside from the fact that such heating results in relatively disadvantageous efficiency and furthermore takes a relative long time, the partial overheating may furthermore lead to destroying particularly susceptible organic reagents at the heat exchange surfaces. Accordingly the temperature control must always take place at low temperature differences, whereby a relatively long time is required to achieve temperature compensation within the liquid. Independently of the part of the liquid container in which the temperature is measured, such temperature measurement is not representative of the average overall liquid temperature. Accordingly, this known method is physically and technically slow, inaccurate and costly in energy, whereby the field of application is becoming increasingly restricted in the presence of the increasing requirements of technology.

In another well known method, the heating takes place by microwaves, however this procedure incurs the essential drawback that the temperature-sensor pickups are affected by the microwave, so that substantial test errors are generated which make it possible to perform temperature control in the sense of regulation.

In a further known method, the heating takes place by means of infrared radiation. Because infrared radiation-intensity decays due to high specific absorption as the depth of penetration into the liquid increases, there occurs local overheating similar to the above described convective heating and with the above-said drawbacks. Again a relatively long time is required for homogeneous heating to occur. Besides the resultant and relatively shallow depth of penetration taking place in this instance, in pure technical terms, infrared temperature control is costly and not universally applicable.

ADVANTAGES OF THE INVENTION

The process of the invention with the characterizing features of the independent claim and also the apparatus of the invention for implementing the invention offer the advantage over the state of the art that the heating takes place homogeneous over the entire cross section subjected to the sound, whereby a partial overheating such as is inevitable in convection heating cannot take place. This is especially significant for biological liquids or such which contain biological substances such as proteins or living cells. Contrary to the case of heating this partial overheating, the homogenizing effect of ultrasonics and thereby the optimal temperature distribution make it possible to prevent denaturing or cell destruction. Illustratively the invention makes it possible in a very simple manner to homogenize and pasteurize milk without danger of overheating.

Another essential advantage is that the ultrasonics is controlled in inertialess manner so that no complex regulating means are required. As a rule a mere proportional control will suffice. Due to the turbulence generated by the acoustic pressure in the liquid, additional agitation is not required and therefore a corresponding agitation means can be dispensed with.

The claims contain a series of embodiments of the invention and are discussed in further detail in the following description of the FIGURES in relation to examples and their advantages.

DRAWING

Four illustrative embodiments of the object of the invention are discussed in closer detail in the drawing and are described comprehensively below:

FIG. 3 shows the second embodiment as a temperature control in laboratory vessels.

FIG. 4 shows the third embodiment as a temperature control in sealed volumes of liquid.

DESCRIPTION OF ILLUSTRATIVE EMBODIMENTS

In all the embodiments described below, the apparatus involved generates ultrasonics and the temperature of controls liquids, each being associated with an electronic means not further described here. These electronic control means operate in known manner by applying the signal of an actual temperature measurement and by using a control program following the comparison with a reference temperature to drive electroacoustic generators, whereby at last the regulation or control of the temperature has been achieved.

Figure 1:
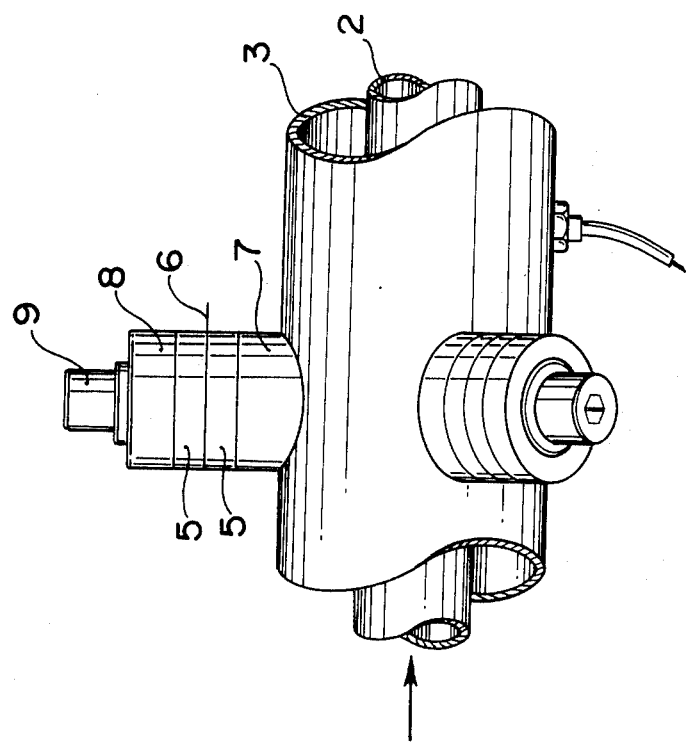
FIGS. 1 and 2 show the first embodiment of an in-line temperature control.
Figure 2:
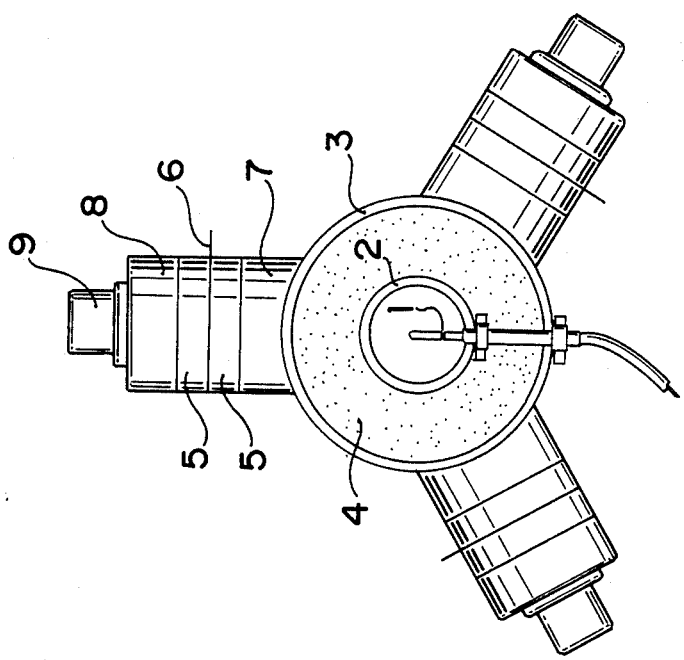

FIGS. 1 and 2 show apparatus by means of which a temperature pickup 1 sensors the actual temperature of the liquid flowing through a tube 2 and to be temperature controlled. A sleeve-shaped reflector 3 is mounted coaxially to this tube 2 with a coupling medium 4 being provided between the tube 2 and sleeve 3. Besides transmitting the sound, the coupling medium also acts as a thermalinsulator, whereby at high temperatures no temperature is transmitted from the oscillation generator following shutoff to the medium to be temperatureee controlled. Obviously no gases can be used as a coupling medium because otherwise there would at once take place total reflection of the ultrasonics.

Three electroacoustically operating ultrasonic, ultrasonic compound oscillators are mounted equally distributed on the periphery of the reflecting member sleeve, each with two electroacoustic transducers 5 between which is mounted a contact disk 6, further with an adaptor 7 pointing towards sleeve 3, further with a sealing member 8 mounted on the other side of the compound oscillator and further screw means 9 holding the parts together. The electroacoustic transducers 5 may consist of a arbitrary number piezoceramic or magnetostrictive or similar parts. The contact disk 6 preferably consists of copper beryllium and acts as a connecting means of the electroacoustic transducers 5 to an electric generator, that is, for driving the ultrasonic generators to their resonant frequency.

As can be seen from FIG. 2 and from the direction of flow of liquid shown therein by the arrow, the temperature pickup 1 is mounted downstream of the ultrasonic oscillators 5–9. Accordingly the actual temperature measured in the tube 2 already can be determined by ultrasonic control. Therefore the intensity and the duration of the ultrasound can be determined by the electronic control for purposes of thermostatic conditions. It is conceivable furthermore that several such units can be mounted sequentially on the tube 2. The resonant frequency can be obtained by selecting suitable materials, dimensions and a number of such compound oscillators, with the homogeneous energy feed-in resulting in the feed tube 2.

Due to the insertion of a coupling medium 4, the resonant phenomena are also made use of in the feed tube 2 or in the coupling medium 4, in order to couple as high as possible a portion of energy.

Due to the star-like arrangement of the ultrasonics compound oscillators (FIG. 1), the effect of ultrasonic focusing by the walls opposite the compound oscillators is utilized. In this manner the ultrasonic wave several times crosses the feed tube several times.

FIG. 3 shows a further embodiment for laboratory use in the form of a "commercial ultrasonics generator". Essentially the design of the apparatus corresponds to the parts 5, 6, 8 and 9 of the above-described embodiment. Merely a radiating horn 10 is provided in lieu of the adaptor 7, where said horn is provided with a radiating surface 11 on the tapered side facing the transducer 5, said surface 11 being oblique to the axis of the apparatus. The entire oscillator then comprises a central and axial bore to receive a cable 12 leading to the temperature pickup one. The radiation horn 10 with the radiation surface 11 is dipped into the liquid to be treated which illustratively is in a laboratory vessel. Optimal ultrasonic treatment of the liquid with minimized losses is achieved by shaping the turbulence-generating surface 11 with respect to the geometry of the laboratory vessel 13. The liquid temperature measured by the temperature pickup 1 in the vessel is fed into the omitted electronic control and there it is compared with the reference volume. In such a laboratory apparatus, this reference volume illustratively can always be set arbitrarily. In accordance with the program receiving for instance a specific control value, the temperature difference between the test and reference values provides a control signal controlling the coupled ultrasonic energy either in the form of ON and OFF switching or as a frequency control in order to achieve thereby a temperature setting which is as accurate and as rapid as possible. Advantageous in this instance the ultrasonic coupling used for heating also is used to agitate the liquid, whereby two functions are implemented with only one apparatus and only one energy source. Because the energy supply in the form of ultrasonics can be controlled in inertialess manner, one can dispense with the otherwise required phase-lead of the temperature at the heating side required in other apparatus. Otherwise there would be the danger of overshooting. Furthermore the oblique radiation surface 11 offers the advantage to generate liquid circulation in the container whereby improved heating in addition to optimal homogeneous mixing will be achieved.

FIG. 4 shows an illustrative embodiment of the object of the invention for treating liquids within such closed vessels as plastic pouches. Such liquids illustratively can be solutions of infusion or preserved blood which require being raised from a low temperature to body temperature, in which procedure they must not be damaged or come into contact with air.

Illustratively in this embodiment as in FIG. 1, two compound oscillators are described which are mounted only on one adaptor 7 which in turn is mounted on a reflection member 3 designed as a reservoir. This reservoir is partly filled with a liquid coupling medium, for instance water. A plastic pouch 15 is suspended into this tank 3, i.e. into the water 14 and is filled with the liquid which must be temperature controlled. In this embodiment the temperature is measured through a window 16 in reservoir 3 using an infrared temperature meter 17. The window 16 may consist of germanium or silicon or of another infrared-transmitting medium. The pouch 15 with the medium to be treated is suspended from a fastening means 18 from above into the reservoir 3.

The infrared meter 17 is preferably designed as a compensation device and measures the liquid temperature in the pouch 15 and compares it with a reference temperature. These infrared-meters (pyrometers) include a pickup (infrared radiation detector) which is raised to the reference temperature for instance using a Pelletier thermostat and which will emit a signal until the medium being tested (actual temperature) has reached the reference temperature. Because most applications concerned cell-liquids, a high frequency is used, so as to avoid cell damage by cavitation. As the density of water and plastic is nearly the same, the transmission of the oscillations from the adaptor 7 through the coupling medium 14 (water) to the temperature controlled medium in the pouch 15 is assured with low losses.

It is known that it is nearly impossible to mix liquids within sealed plastic pouches, and accordingly precisely in this embodiment, the characteristic of ultrasonics in homogenizing liquids is decisive.

Figure 5:
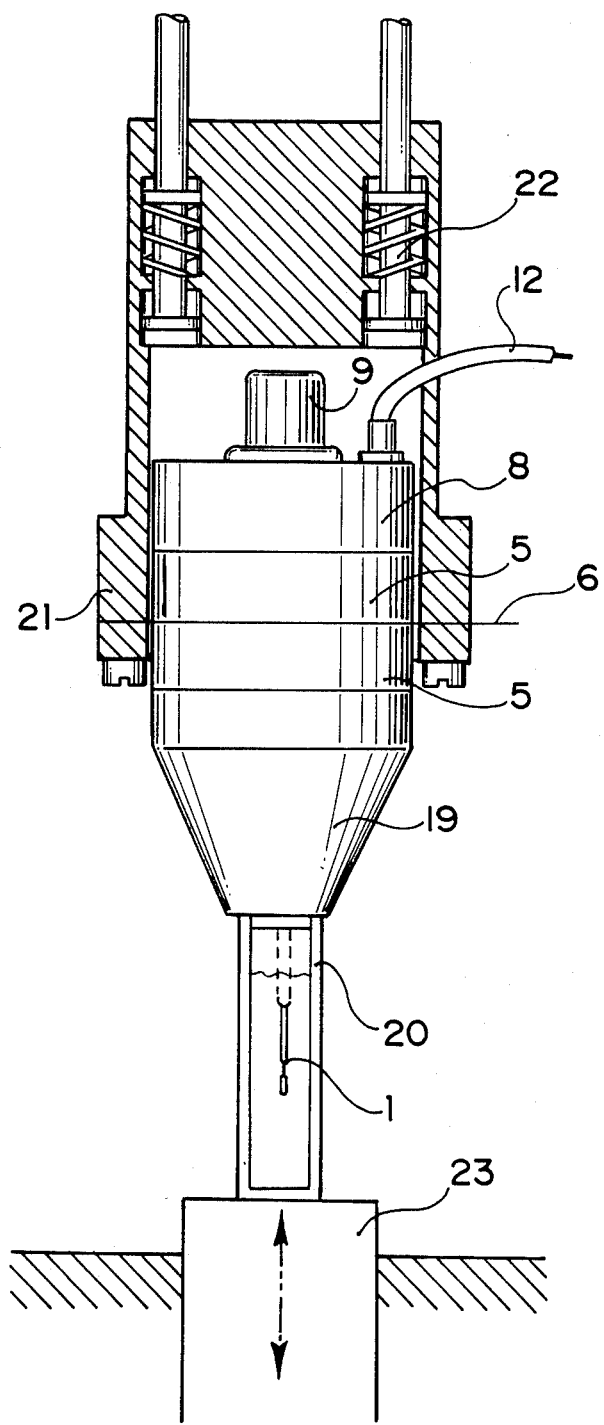
FIG. 5 shows the fourth embodiment as a temperature control through energizing the wall of a cut-shaped container.

In the fourth embodiment shown in FIG. 5, a compound oscillator is designed in principle to be the same as in the second embodiment (FIG. 3) and comprises a coaxial temperature pickup, being designed to achieve temperature control by driving the container walls into oscillation. The radiator or adaptor 19 is connected to the electric acoustic transducer 5, where the adaptor side away from the transducer is fitted to the shape of a container 20. This container may be a cuvette open at the top used for photometric testing in the clinical-chemical or biochemical field. The compound oscillator for that purpose is fixed in a support 21 for instance by means of the contact disk 6, where the support 21 itself is suspended from an element 22 compensating the path oscillation. A compressing device 23 positively forces the container 20 against the radiation member 19.

The oscillations generate intensive turbulence, most of all at the container's walls and corners where no flow can be generated when the conventional agitation methods are used. Due to the ultrasonic oscillation transmitted to the container 20, homogenization and uniform heating of the liquid take place, so that in principle the test point can be anywhere in the container. Obviously also the temperaure can be measured by optic means in lieu of a pickup 1 making physical contact. In any event, the ultrasonic effect makes possible a temperature measurement-accuracy of 0.01 degrees C. or better. This is especially significant in reaction-kinetic research where the error in temperature proportionately limits the possible accurracy of analysis and the synchronization of automatic equipment.

Not only as regards the examples shown above but quite in general the temperature effect of the invention can be obtained by turning ON and OFF the ultrasonic or also by changing the amplitude of oscillation.

We claim:

1. A process for controlling the temperature of a liquid comprising:
   providing acoustic ultrasonic wave generating means, responsive to a control signal, for generating acoustic ultrasonic waves to substantially homogeneously heat a liquid;
   irradiating at least a portion of said liquid with acoustic ultrasonic waves from said acoustic ultrasonic wave generating means to substantially homogeneously heat said at least a portion of said liquid;
   providing temperature sensing means for measuring the temperature of said heated liquid;
   measuring the temperature of said heated liquid with said temperature sensing means to obtain an actual temperature of said liquid;
   providing electronic control means, operably connected to said acoustic ultrasonic wave generating means and said temperature sensing means, for comparing said actual temperature of said heated liquid with a predetermined desired temperature of said heated liquid and producing a control signal based on said comparison;
   comparing said actual temperature of said heated liquid with a predetermined desired temperature of said heated liquid and producing a control signal based on said comparison;
   feeding said control signal to said acoustic ultrasonic wave generating means.

2. The process according to claim 1, wherein said temperature sensing means comprises a sensor immersed within said liquid.

3. The process according to claim 1, wherein said temperature sensing means comprises an optical temperature sensing means for measuring temperature in a contactless manner.

4. The process according to claim 1, wherein said liquid is disposed within a container and said acoustic ultrasonic wave generating means is coupled to said container through a coupling medium.

5. The process according to claim 4, wherein said coupling medium is a liquid.

6. The process according to claim 5, wherein said liquid is water.

7. The process according to claim 4, wherein said coupling medium is an elastic, thermal insulating material.

8. The process according to claim 4, wherein said container is a liquid conduit and said liquid is flowing through said conduit.

9. The process according to claim 4, wherein said container is a sealed container.

10. The process according to claim 1, wherein said liquid is disposed within a container and said acoustic ultrasonic wave generating means is directly coupled to said container.

11. The process according to claim 1, wherein said liquid is disposed within a container and said acoustic ultrasonic wave generating means is in direct contact with said liquid.

* * * * *